United States Patent [19]
Brannon

[11] Patent Number: 6,007,496
[45] Date of Patent: Dec. 28, 1999

[54] SYRINGE ASSEMBLY FOR HARVESTING BONE

[76] Inventor: James K. Brannon, 5729 Canterbury Dr, Culver City, Calif. 90230

[21] Appl. No.: 08/774,799

[22] Filed: Dec. 30, 1996

[51] Int. Cl.⁶ .................................................. A61B 10/00
[52] U.S. Cl. .......................... 600/565; 600/566; 600/564; 600/567; 606/185
[58] Field of Search .................................... 600/562, 564, 600/566, 567; 606/79, 80, 170, 167, 184, 53, 61, 82, 84, 86, 87, 88, 96; 604/22, 164; 623/16

[56] References Cited

U.S. PATENT DOCUMENTS

| | | | |
|---|---|---|---|
| 3,750,667 | 8/1973 | Pshenichny et al. | 604/164 |
| 4,513,754 | 4/1985 | Lee | 600/566 |
| 4,838,282 | 6/1989 | Strasser et al. | 600/567 |
| 5,005,585 | 4/1991 | Maza | 600/567 |
| 5,152,763 | 10/1992 | Johnson | 606/86 |
| 5,197,967 | 3/1993 | Wilson | 606/79 |
| 5,269,785 | 12/1993 | Bonutti | 606/80 |
| 5,409,463 | 4/1995 | Thomas et al. | 604/167 |
| 5,515,861 | 5/1996 | Smith | 600/567 |
| 5,556,399 | 9/1996 | Huebner | 606/80 |
| 5,632,747 | 5/1997 | Scarborough et al. | 606/79 |
| 5,662,615 | 9/1997 | Blake, III | 604/164 |
| 5,683,406 | 11/1997 | Altobelli et al. | 606/170 |
| 5,720,748 | 2/1998 | Kuslich et al. | 606/80 |
| 5,741,253 | 4/1998 | Michelson | 606/61 |
| 5,782,835 | 7/1998 | Hart et al. | 606/79 |
| 5,800,398 | 9/1998 | Hahnle et al. | 604/164 |
| 5,833,628 | 11/1998 | Yuan et al. | 600/567 |
| 5,868,684 | 2/1999 | Akerfeldt et al. | 600/564 |

OTHER PUBLICATIONS

Anderson, M.D., Michael J., et al., Compressive Mechanical Properties of Human Cancellous Bone, JBJS 75–A Jun. 1992, 747–752.

Billmire, M.D., David A., et al., Ideas and Innovation: Use of The Corb Needle Biopsy for The Harvesting of Iliac Crest Bone Graft, Plastic and Reconstructive Surgery, Feb. 1994.

Saleh, Michael, Bone Graft Harvesting: A Percutaneous Technique, JBJS [BR.], 1991; 73–B: 867–868.

Innovasive Devices Innovasive COR™System, Brochure 734 Forest Street, Marlborough, MA 01752, Sep. 1996.

Arthrex, Osteocrondral Autograft Transfer System (Oats)™ Brochure, 2885 South Horseshoe Drive, Naples, Florida 34104.

*Primary Examiner*—Richard J. Apley
*Assistant Examiner*—Justine R. Yu
*Attorney, Agent, or Firm*—Lyon & Lyon LLP

[57] ABSTRACT

A device for harvesting bone, including a hollow cylindrical rod having a sharpened distal end, a proximal end with a handle thereon, and a chamber therein extending axially between the proximal and distal ends. A plunger rod is inserted into the proximal end of the cylindrical rod, the plunger rod being slidable axially within the chamber. A sealing support is provided on the proximal end of the hollow cylindrical rod for engaging the plunger rod to establish a slidable hermetic seal therebetween and prevent retrograde flow of air into the chamber from the proximal end of the cylindrical rod. The device also includes a side opening in the cylindrical rod communicating with the chamber, which is connectable to a source of vacuum for evacuating fluid from the chamber into a fluid reservoir connectable to the side opening for collecting fluid therein.

16 Claims, 7 Drawing Sheets

SYRINGE ASSEMBLY FOR HARVESTING BONE

BACKGROUND OF THE INVENTION

1. Field of the Invention

Bone grafting is among one of the most frequently performed surgical procedures by surgeons challenged with reconstructing or replacing skeletal defects. Over the years, several techniques have been devised to obtain and implant autologous bone. Scientist and clinicians have sought and defined the essential elements of bone healing and have further desired to secure these elements when considering the benefits of various types of bone grafting techniques. The essential elements required for bone regeneration are osteoconduction, osteoinduction, and osteogenic cells. In this regard, autogenous bone is the gold standard for bone harvesting. Cancellous bone contains all of these elements but lacks structural integrity. Cortical bone has structural integrity but is limited in quantity. Further, clinicians have recognized the consequences of donor site morbidity and prolonged hospitalization. To circumvent some of these issues, numerous synthetic bone like products have been made available for general use. Each product attempts to exploit one or more of the three essential elements of bone regeneration described above. Although many of these products, e.g., Pro Osteon, INTERPORE, Collagraft, ZIMMER, and others are unique, they all are very expensive and continue to escape the concepts of healthcare reform: A standard of care, with standard products, at a standard cost.©

To define a less invasive technique for bone harvesting, percutaneous methods have been described. The recently developed techniques simply involve using a coring cylindrical device to obtain a segment of bone. David Billmire, M.D. describes this technique in his article, Use of the CORB Needle Biopsy for the Harvesting of Iliac Crest Bone Graft, PLASTIC AND RECONSTRUCTIVE SURGERY, February 1994. Billmire makes no effort to ensure the quality of the harvested bone but rather describes a power-driven counter-rotating hollow needle as cutting through bone and soft tissue. Michael Saleh describes a percutaneous technique for bone harvesting in his article, Bone Graft Harvesting: A percutaneous Technique, *Journal of Bone and Joint Surgery* [*Br*] 1991; 73-B: 867-8. The author describes using a trephine to twist and lever out a core of bone of 8 mm in size. INNOVASIVE DEVICES describes using their COR™ System for arthroscopic bone graft harvesting. This system describes a disposable cutter having a distal cutting tooth projected into the lumen of the Harvester. This cutting tooth ensures that all harvested osteochondral bone grafts taken will be a uniform depth. This cutting tool also serves as means for removing the harvested bone from its donor site. Further, the plunger of the COR™ System is used to gently disengage the harvested bone so as to maintain the overall height of the graft. This concept is absolutely essential to the successful use of the COR™ System as these precisely obtained samples of osteochondral bone are implanted into pre-drilled osteochondral defects within the knee. Further, a vacuum of any sort could not be used on the COR™ System as the vacuum would simply continue to extract water from the knee joint, thereby failing to create an effective pressure drop across the harvested bone, and loss of operative visualization.

When considering bone for grafting purposes, the recipient site must be considered as well. Failure to achieve bony union at a fracture site may be caused by several reasons. Frequently, the blood flow is inadequate in the fracture area as a consequence of local trauma during the inciting event. Thus, when considering augmentation of the healing process with bone graft, it is imperative that the grafted bone contain all of the essential elements germane to successful osseous regeneration, namely, osteoconductive elements, osteoinductive elements, and osteoprogenitor cells. All current devices used for bone grafting focus on quantity, the osteoconductive portion of the harvested bone, and not quality, the osteoinductive portion of the harvested bone. Bone is viscoelastic, see below, and includes elements that are both elastic, osteoconductive, and viscous, osteoinductive. The osteoprogenitor cells and various proteins are within this viscous fluid state. Therefore, any device used to harvest bone to promote osseous union must consider the issues of osteoconduction, osteoinduction, and osteoprogenitor cells. Regarding cancerous bone, these fluid elements are within the interstices of the bone.

2. Information Disclosure Statement

To recognize the issues at hand governing the invention described herein, a simple discussion of biomechanics, physiology, and some general physics is warranted and presented in support hereof.

Bone is a viscoelastic material, and as such, it behaves predictably along its stress strain curve when axially loaded in either tension or compression. The key word here is viscoelastic. The prefix "visco" describes the fluid component of the material being tested and the suffix "elastic" describes the recoil potential of the material being tested. The ratio of stress:strain is Young's Modulus. Clearly, a spring is fully elastic. One may place a tension force on a spring, but when the tension is released, the spring recoils to its original length. A syringe, on the other hand, with a thin hypodermic needle attached, is considered viscoelastic. In other words, the amount of deformation observed is time dependent. Simply, the deformation will remain after the tension is removed. Consider one throwing Silly Putty against the ground and observing it bounce versus letting the material sit on a counter for several hours. One should appreciate that minimal deformation occurs when the Silly Putty bounces from the floor versus sitting on a counter for several hours. The deformation is time dependent as a consequence of the internal fluid properties of the material, an amount of time is required to observe a net fluid flow. Bone behaves in a similar fashion, but has the additional property of being able to respond to a given stress by forming new bone. When bone fails to respond favorably, it fractures.

The physiologic properties of bone hinge on the fluid elements that govern bone regeneration, namely, bone morphogenic protein, various hormones, and osteoprogenitor cells. These fluid elements are integral to the physiologic function of bone and are found within the bone marrow and the circulatory system. Appreciate that there is a net flow of these elements as bone bares a daily physiologic load during normal walking. Since the circulatory system is a closed system, a net loss of these fluid elements is not observed but rather metabolic maintenance of the various cells and proteins as they age and become nonfunctional.

Bone is incompressible above or below its elastic limit, i.e., Young's Modulus. Poisson's ratio is used to describe this behavior and can be defined as follows:

$$\nu = -(\Delta d/d_0)/(\Delta l/l_0) \quad (1),$$

Poisson's ratio can be thought of as a measure of how much a material thins when it is stretched, consider taffy, or how much a material bulges when it is compressed. Regarding bone, one does not necessarily observe an increase in volume when it is compressed, but rather an increase in the density as bone remodels along the lines of stress, i.e., form follows function, Wolff's Law. When bone is compressed beyond its elastic limit, it fractures, therefore, its area will increase in a direction perpendicular to the line of force. The fracture observed occurs in the osteoconductive portion of bone, and a fluid flow will occur within the osteoinductive portion of bone having the osteoprogenitor cells.

When obtaining autogenous bone for grafting, one should have an appreciation for the above principles as they will govern the quality of the bone graft material obtained. Additionally, traditional open techniques involve uncontrolled morselization of the bone graft material, thereby decreasing the amount of harvested osteoconductive bone for grafting purposes. The invention described herein exploits these principles uniquely so as to obtain unequivocally the optimum quantity and quality of bone graft material. The inventor recognizes the desire of all clinicians to eliminate donor site morbidity and promote rapid osseous incorporation of the grafted material at the recipient site. Importantly, these noble objectives will be tempered by healthcare reform.

SUMMARY AND OBJECTS OF THE PRESENT INVENTION

It is and object of the present invention to provide a method for percutaneously obtaining a large volume of cancerous bone for bone grafting.

It is yet a further object of the present invention to provide means for processing a volume of harvested bone.

It is yet a further object of the present invention to ensure that the harvested bone retains all of the essential elements deemed necessary for rapid osseous incorporation of autogenous bone graft.

It is yet a further object of the present invention to decrease donor site morbidity.

It is yet a further object of the invention to promote all musculoskeletal surgeons to use natural bone when bone grafting is required for oseous regeneration.

It is yet a further object of the present invention to completely standardize the art of iliac crest bone grafting so as to promote cost savings.

SUMMARY

The invention describes a novel and unobvious method for processing harvested bone. A hollow cylindrical rod is percutaneously inserted into the pelvis at the level of the anterior and superior iliac spine. The cylinder of the syringe apparatus is forcibly passed into the substance of cancellous bone with the distal end of the cylinder sharpened to a degree so as to facilitate its insertion and minimization of morselization of the bone. This insertion is within the horizontal plane and runs obliquely to the coronal and saggital planes. During insertion, a bone plug piston is created. This autologous bone plug piston contains all of the essential elements required for successful bone regeneration. A plunger rod is then inserted into the cylinder through a proximal opening of the cylinder. A slidable fluid seal engages the proximal portion of the plunger rod as the outer diameter of the plunger rod is smaller than the internal diameter of the cylinder. Now with the bone plug piston in place, and the cylinder coaxially engaging the plunger rod, a functional syringe is operational for the purpose of processing the autologous bone plug piston. A proximal side opening of the cylinder allows for the attachment of a vacuum type device so as to maintain a constant pressure drop across the bone plug piston. One may gently increase the pressure drop across the bone plug piston by advancing the plunger rod proximally. In so doing, the viscous elements of bone are caused to flow proximally. This proximal flow is of a gentle degree so as not to cause hemolysis of the formed elements of blood. Alternately, as one begins to compress the bone plug piston beyond its elastic limit by advancing the plunger rod distally, the bone plug piston will fracture and collapse. In so doing, the collapsed bone will attempt to expand within the coring cylinder. Given the physical constraints of the coring cylinder, the bone will expand slightly and increase the frictional force between the bone plug piston and the inner wall of the coring cylinder. The remaining force imparted by the plunger rod will cause a net fluid flow of the viscous elements of the bone plug piston. Given that a pressure drop is maintained across the bone plug piston, a net flow of the intraosseous blood in the proximal direction will occur. This flow direction will ensure that the bone plug piston contains all of the essential elements of bone regeneration. A collecting reservoir is provided to collect any residual blood not contained with the bone plug piston. Inherent to this system is a requirement for a gentle viscous flow of the blood so as not to cause lysis of any of the formed elements of blood as described above. Appreciating the physics at one, one might consider decreasing the mass of the plunger as Newton's second law shows that a force F is directly proportional to a mass m times acceleration a. Doing so allows one to exert a minimal amount of force over the compression surface of a viscoelastic bone plug piston. This concept may have significance while harvesting cartilage.

DESCRIPTION OF THE PREFERRED EMBODIMENTS

Figure 1:
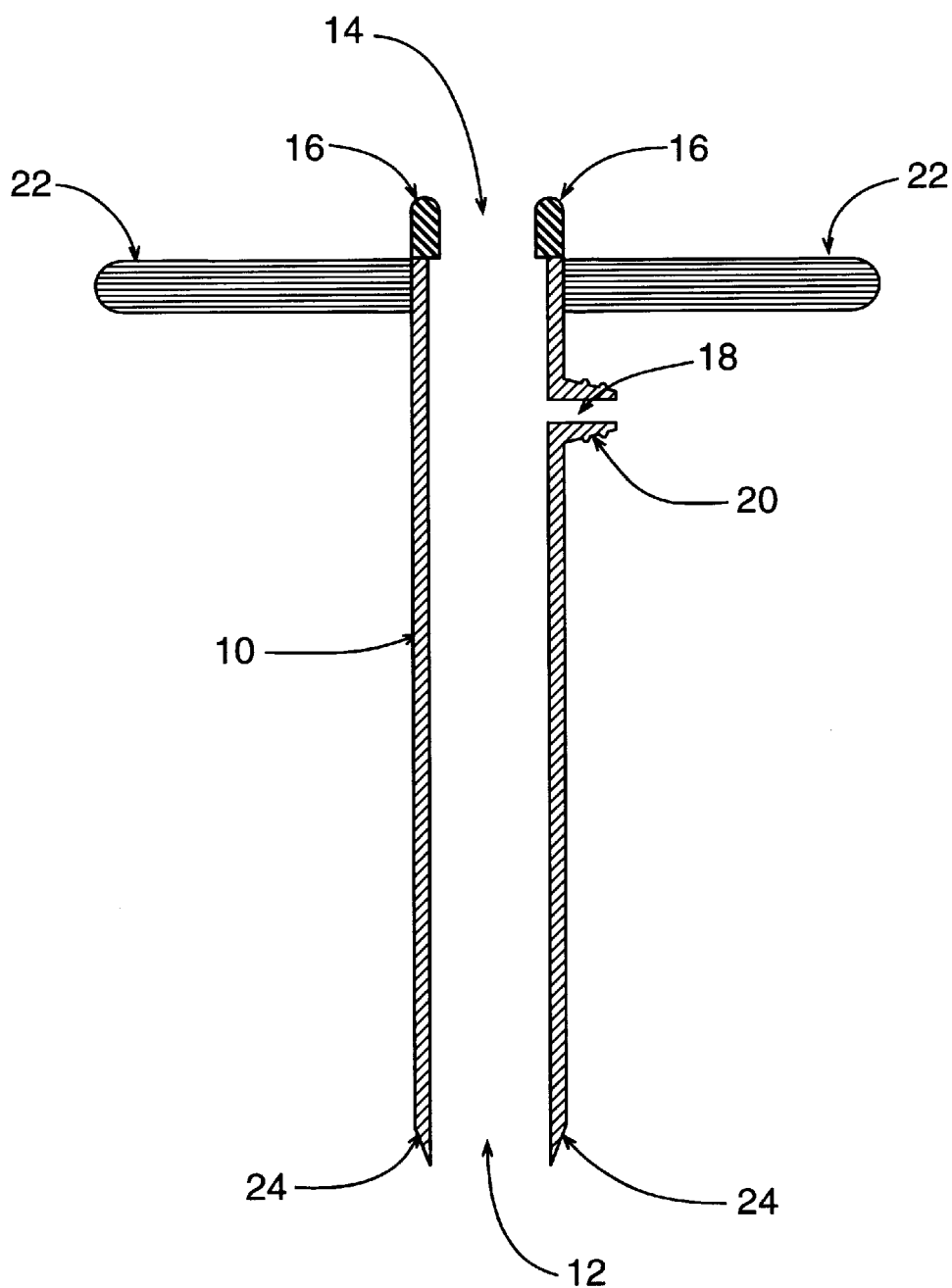
FIG. 1 is a sectional view of the cylinder of the present invention.

There shown generally at 8 in FIG. 1 is a cylinder 10 having a proximal opening 14 and a distal opening 12. The distal opening 12 further has a sharpened edge 24. Circumferential to the proximal opening 14 is a sealing support 16. Positioned proximally is a partial opening 18 having a portion 20 of a size and shape adapted for mounting a vacuum tube 38. A cross handle 22 is attached to the cylinder 10 to facilitate operation of the bone harvesting syringe.

Figure 2:
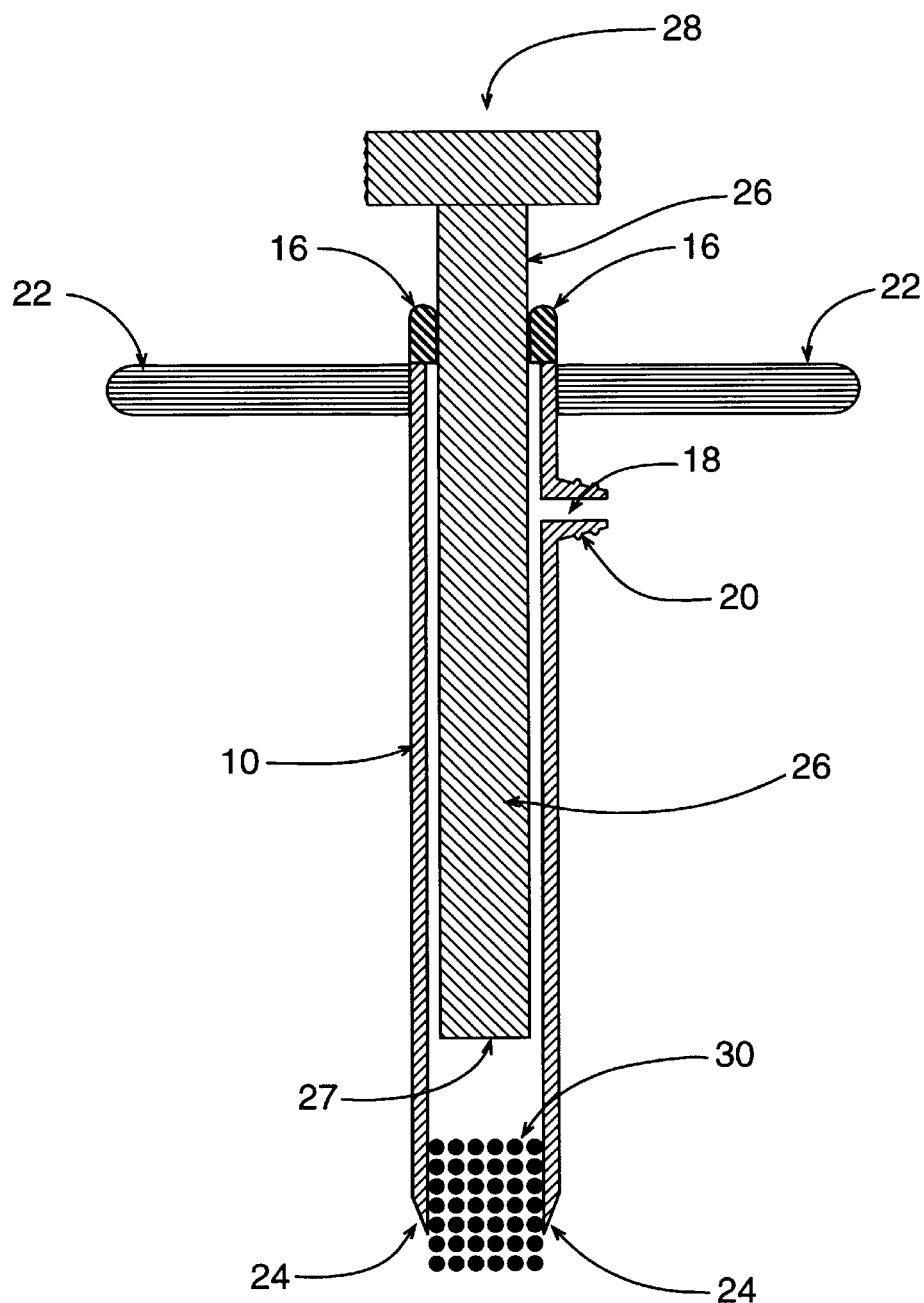
FIG. 2 is a sectional view of the cylinder, the bone plug piston, and the plunger. The bone plug piston has not been processed.
Figure 3:
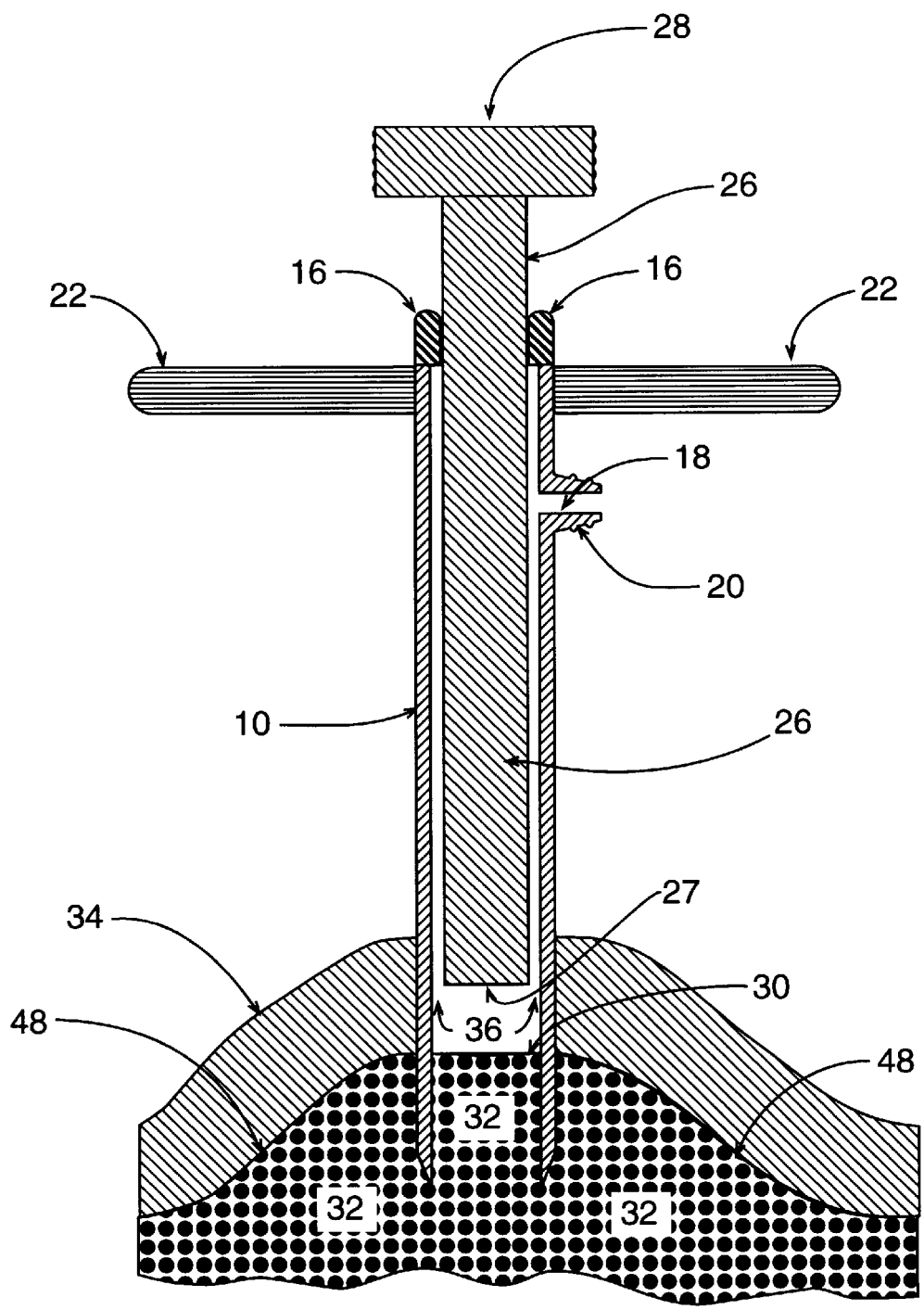
FIG. 3 shows the bone harvesting syringe in use. The harvesting syringe has been percutaneously inserted into the pelvic bone other appropriate bone grafting site.
Figure 4:
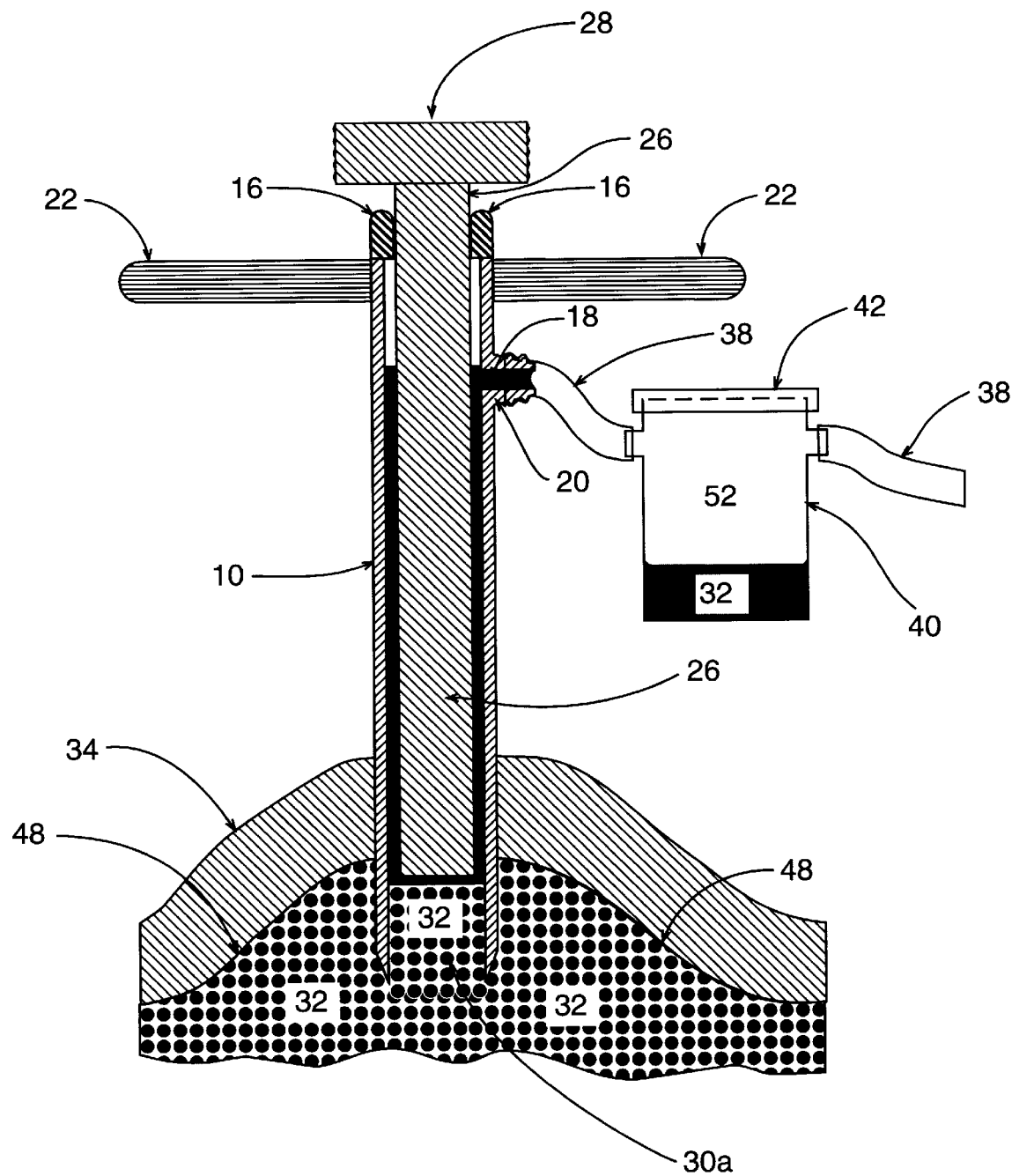
FIG. 4 shows the processing of the bone plug piston. The plunger compresses the bone plug piston. The fluid reservoir serves as a collection site for the excess viscous elements of bone.

FIG. 2 shows the completed assembly with a plunger 26 having a thumb rest 28 coaxially engaged by the cylinder 10. A slidable hermetic fluid seal is established at the interface between the sealing support 16 and the plunger 26. A viscoelastic bone plug piston 30 is engaged by the distal opening 12 of the cylinder 10. FIG. 3 shows the device of this invention having been percutaneously inserted through the skin 34 and into the surrounding bone 48. The sharpened edge 24 facilitates advancement of the cylinder 10 into the bone and minimizes morselization of the surrounding bone 48. A viscoelastic bone plug piston is created within the distal end of the cylinder 10. The plunger 26 is slidable within the cylinder 10 and creates a fluid chamber 36 circumferential to the plunger 26. FIG. 4 shows the processing of the viscoelastic bone plug piston. A viscous osteoinductive fluid 32 containing osteoprogenitor cells is within the substance of the viscoelastic bone plug piston 30. An axial load is applied to viscoelastic bone plug piston 30 by a substantially flat distal surface 27 of the plunger 26 to create a processed osteopiston 30a.

Figure 5:
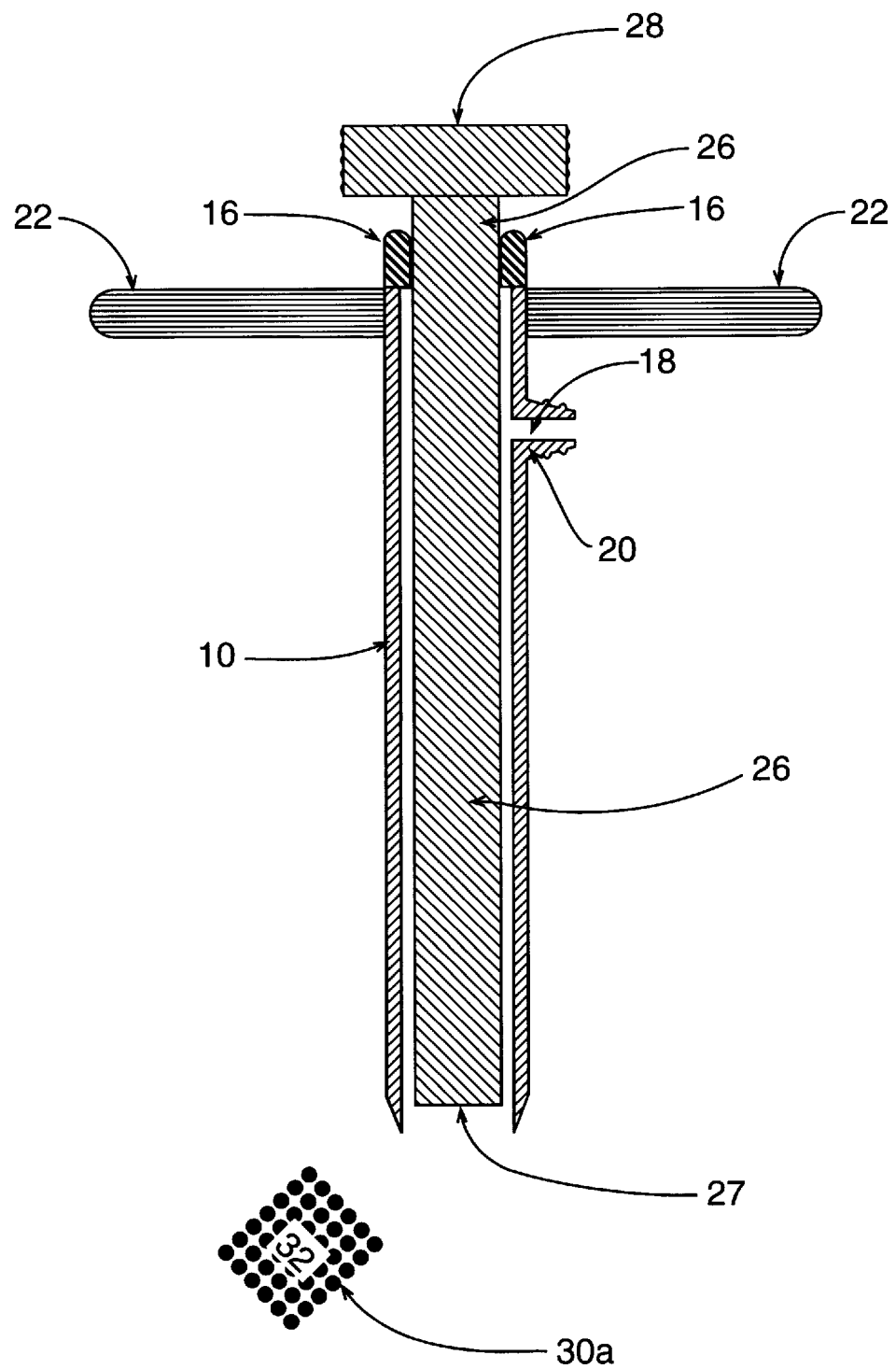
FIG. 5 shows the bone harvesting syringe having been removed from the donor site with the bone plug piston having been dislodged from the cylinder.

The processed osteopiston 30a forcibly expands within the distal end of the cylinder 10. This expansion will incarcerate the processed osteopiston 30a within the distal end of the cylinder 10 along a distal inner wall 50 and cause a net fluid flow of the osteoinductive elements of the harvested bone. The vacuum tube 38 creates a pressure drop across the processed osteopiston 30a and causes the preferential proximal flow of the viscous osteoinductive fluid 32 when the plunger 26 compresses the processed osteopiston 30a. The pressure drop is of a magnitude to induce a gentle flow of the osteoinductive elements of bone so as to substantially prevent the hemolysis of the osteoprogenitor cells. An additional proximal flow can be obtained by advancing the plunger 26 proximally. A fluid reservoir is interposed within the suction tube 38 so as to collect the osteoinductive fluid of the harvested bone. This fluid can be used to further augment the bone graft. After processing the viscoelastic bone plug piston 30, one simply rotates the cylinder 10 clockwise or counter clockwise so as to disengage the cylinder 10 from the surrounding bone 48. FIG. 5 shows the processed osteopiston 30a having been dislodged from the cylinder 10 by simply advancing the plunger 26 distally. The processed osteopiston 30a containing all of the viscous osteoinductive fluid 32 can now be implanted into the recipient site.

Figure 6:
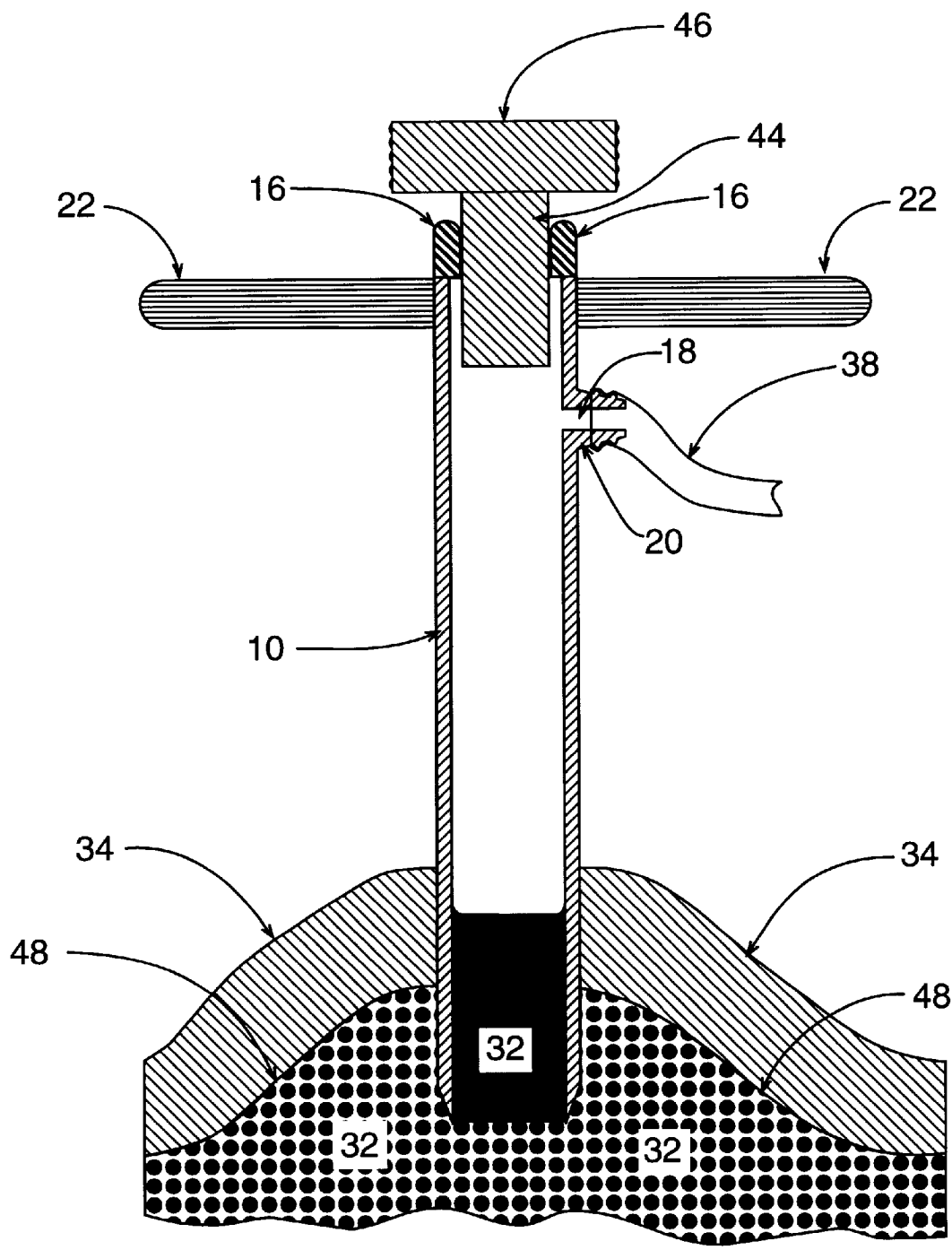
FIG. 6 shows the device of this invention being used as a suction tool to facilitate the collection of blood from the donor site and small fragments of bone. A short plunger is used to plug the proximal hole of the cylinder.

FIG. 6 simply shows the device of this invention being used as a suction tool to evacuate any residual viscous osteoinductive fluid 32. A stopper 44 having a thumb rest 46 is sealably engaged in the proximal end of the cylinder 10. The fluid reservoir 40 serves as a collector of the residual viscous osteoinductive fluid 32. This residual fluid may be used to further augment the bone regeneration process.

Figure 7:
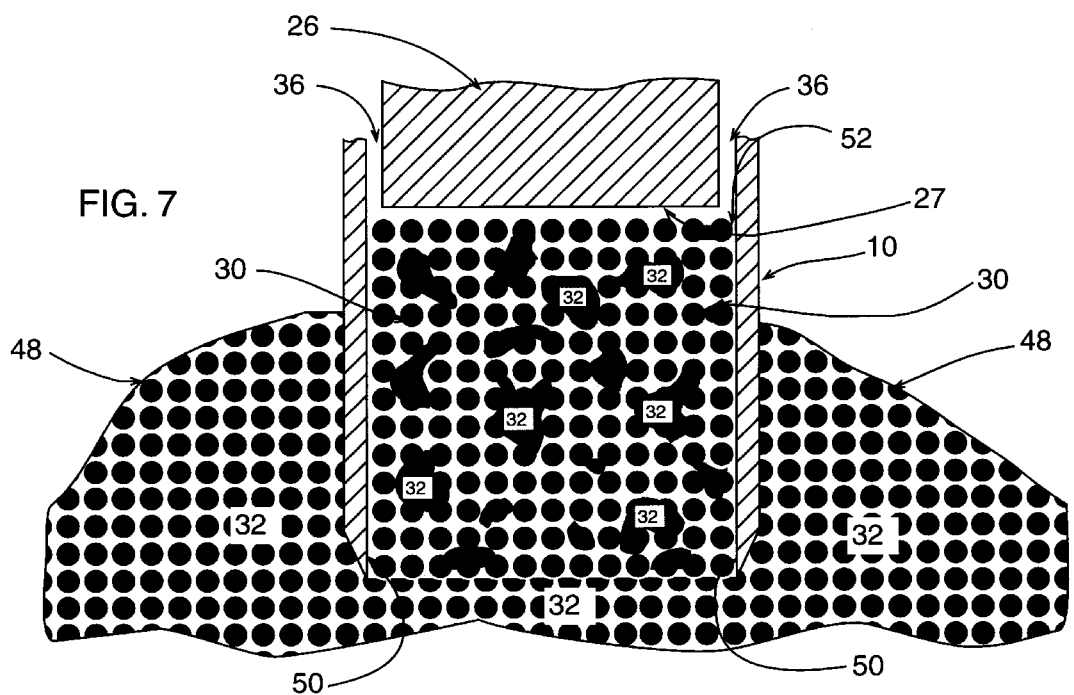
FIG. 7 shows the unprocessed viscoelastic bone plug piston, cancerous bone, with a viscous osteoinductive fluid within its interstices.
Figure 8:
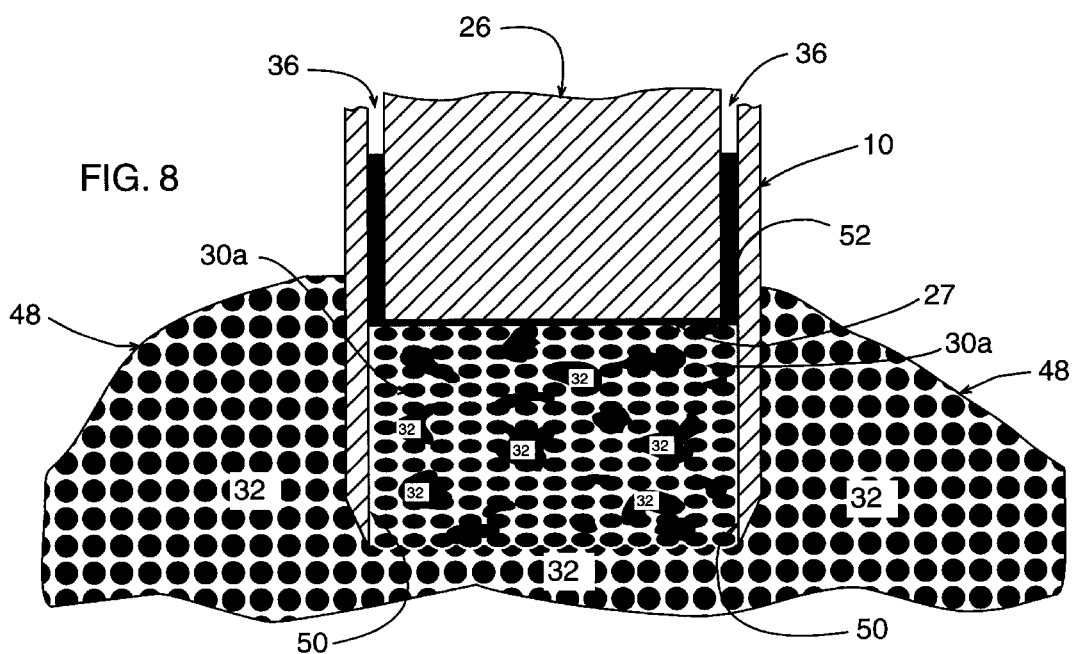
FIG. 8 shows the processed viscoelastic bone plug piston, compact cancerous bone, with a viscous osteoinductive fluid with its interstices. The plunger of FIG. 4 compresses the bone plug piston.

FIGS. 7 and 8 are microscopic representations of the harvested bone. One should generally appreciate that the cancellous bone expands as it is forcibly fractured with the substantially flat distal surface 27 of the plunger 26. This local expansion increases the frictional force experienced at the juncture of the osteopiston and an inner wall 50 of the cylinder 10 thereby allowing one to deliver the harvested bone from the surrounding bone 48 without excessive motion of the cylinder 10. During expansion of the viscoelastic bone plug piston, a net fluid flow of the viscous osteoinductive elements occurs preferentially in a proximal direction secondary to a pressure drop 52 across the viscoelastic bone plug piston. An additional pressure drop may be created by advancing the plunger 26 proximally.

The invention at hand is a very unique way of obtaining a large amount of cancellous bone for grafting. It ensures that the harvested bone retains all of the essential elements of bone regeneration, namely osteoconductive elements, osteoinductive elements, and osteoprogenitor cells. The simple concept emphasizes patient comfort through a percutaneous technique thereby encouraging its use. This technique of harvesting bone should unequivocally replace all synthetic bone material. Indeed, these efforts are in parallel with healthcare reform.

Thus having described the invention at hand, what I desire to claim and secure by Letters Patent is:

1. A syringe assembly for harvesting an osteopiston of bone comprising:

(a) a cylindrical body having an open distal end, an open proximal end, and a proximal inner wall, said open distal end being adapted to receive an osteopiston therein, the osteopiston including a proximal compression face and a distal bone pedicle face, the osteopiston further including a longitudinal friction face for slidably engaging a distal inner wall of said cylindrical body, said distal inner wall having a size and shape adapted to induce a first frictional force against the longitudinal friction face, said distal inner wall having a size and shape adapted to minimize morselization of the osteopiston; and (b) a plunger coaxially engaged by said cylindrical body, said plunger including a distal surface, a longitudinal surface, and a proximal surface, said plunger defining a first fluid chamber between said distal surface and the proximal compression face of the osteopiston, said plunger further defining a second fluid chamber between said longitudinal surface and the proximal inner wall of said cylindrical body, said plunger having a size and shape adapted for compressing and fracturing the osteopiston within said open distal end, whereby the osteopiston substantially engages said distal inner wall of said cylindrical body so as to substantially prevent disengagement of the osteopiston from within said open distal end, said plunger further having a size and shape adapted to impart a pressure gradient across the osteopiston when said plunger is directed axially, said plunger further having a size and shape adapted to induce the gentle flow of a viscous fluid into said first and second fluid chambers so as to substantially prevent the hemolysis of osteoprogenitor cells, wherein said cylindrical body further includes a side opening in said longitudinal surface thereof for evacuating the viscous fluid from within said first and said second fluid chambers.

2. A syringe assembly as defined in claim 1 wherein said cylindrical body further includes a sealing support operationally disposed about the open proximal end of said cylindrical body, said sealing support engaging said plunger along said longitudinal surface so as to substantially prevent the flow of the viscous fluid through said open proximal end at all times when said syringe assembly is in use.

3. A syringe as defined in claim 1 wherein said side opening has a size and shape adapted for mounting a vacuum apparatus, said vacuum apparatus comprising an elongated tube having a collection chamber integral therewith, said vacuum apparatus inducing a pressure drop across the osteopiston so as to ensure the preferential proximal flow of the viscous fluid through said first and said second fluid chambers and into said collection chamber.

4. A syringe assembly for harvesting a viscoelastic bone plug piston comprising:
 (a) a cylindrical body having an open distal end, an open proximal end, and a proximal inner wall, said open distal end being adapted to receive a viscoelastic bone plug piston therein, the viscoelastic bone plug piston including a proximal compression face and a distal bone pedicle face, the viscoelastic bone plug piston further including a longitudinal friction face for slidably engaging a distal inner wall of said cylindrical body, said distal inner wall having a size and shape adapted to induce a first frictional force against the longitudinal friction face, said open distal end having a size and shape adapted to minimize morselization of the viscoelastic bone plug piston; and
 (b) plunger means for inducing a pressure gradient across the viscoelastic bone plug piston so as to cause to separate a viscous fluid therefrom, said plunger means including a distal surface, a longitudinal surface, and a proximal surface, said plunger means defining a first fluid chamber between said distal surface and the proximal compression face of the viscoelastic bone plug piston, said plunger means further defining a second fluid chamber between said longitudinal surface and the proximal inner wall of said cylindrical body, said plunger means having a size and shape adapted for compressing and fracturing the viscoelastic bone plug piston within said open distal end, whereby the viscoelastic bone plug piston substantially engages said distal inner wall of said cylindrical body so as to substantially prevent disengagement of the viscoelastic bone plug piston from within said open distal end, said plunger means further having a size and shape adapted to allow the flow of said viscous fluid into said first and said second fluid chambers;
 wherein said cylindrical body further includes a side opening in the longitudinal surface thereof for evacuating the viscous fluid from within said first and said second fluid chambers.

5. A syringe assembly as defined in claim 4 wherein said plunger means further includes a sealing support on said proximal end of said cylindrical body, said sealing support substantially preventing retrograde flow of air into said cylindrical body, said sealing support engaging said plunger means along said longitudinal surface so as to substantially prevent flow of the viscous fluid through said open proximal end.

6. A syringe as defined in claim 4 wherein said side opening has a size and shape adapted for mounting vacuum means, said vacuum means inducing a pressure drop across the viscoelastic bone plug piston, said vacuum means comprising an elongated tube having a collection chamber integral therewith, said vacuum means further inducing the preferential proximal flow of the viscous fluid through said first and said second fluid chambers and into said collection chamber.

7. A syringe assembly for harvesting a viscoelastic bone plug piston comprising:
 (a) a cylindrical body having an open distal end, an open proximal end, and a proximal inner wall, said open distal end being adapted to receive a viscoelastic bone plug piston therein, the viscoelastic bone plug piston including a proximal compression face, a distal bone pedicle face and a longitudinal friction face, the viscoelastic bone plug piston slidably engaging a distal inner wall of said cylindrical body, said distal inner wall having a size and shape adapted to induce a first frictional force against the longitudinal friction face; and
 (b) plunger means for compressing the viscoelastic bone plug piston within the open distal end of said cylindrical body, said plunger means including a distal surface, a longitudinal surface, and a proximal surface, said plunger means defining a first fluid chamber between said distal surface and the proximal compression face of the viscoelastic bone plug piston, said plunger means further defining a second fluid chamber between said longitudinal surface and the proximal inner wall of said cylindrical body, said plunger means having a size and shape adapted for compressing the viscoelastic bone plug piston into engagement with said distal inner wall of said cylindrical body to substantially prevent disengagement of the viscoelastic bone plug piston from within said open distal end, said plunger means further having a size and shape adapted to induce a pressure gradient across the viscoelastic bone plug piston when said plunger is directed axially so as to cause the flow of a viscous fluid therefrom into one of said first and second fluid chambers;
 wherein said cylindrical body further includes a sealing support on said proximal end of said cylindrical body, said sealing support substantially preventing retrograde flow of air into said cylindrical body, said sealing support sealingly engaging said plunger means along said longitudinal surface so as to substantially prevent flow of the viscous fluid through said open proximal end;
 wherein said cylindrical body further includes means for evacuating the viscous fluid from said cylindrical body, said evacuating means comprising an opening in said longitudinal surface of said cylindrical body.

8. A syringe assembly as defined in claim 7 wherein said opening includes a portion of a size and shape adapted for mounting vacuum means, said vacuum means comprising an elongated tube having a collection chamber integral therewith, said vacuum means inducing a pressure drop across the viscoelastic bone plug piston so as to ensure preferential proximal flow of the viscous fluid through said first and said second fluid chambers and into said collection chamber.

9. A syringe assembly for harvesting a viscoelastic bone plug piston comprising:
 (a) a cylindrical body having an open distal end, an open proximal end, and a proximal inner wall, said open distal end being adapted to receive a viscoelastic bone plug piston therein, the viscoelastic bone plug piston including a proximal compression face, a longitudinal friction face, and a distal bone pedicle face, the viscoelastic bone plug piston slidably engaging a distal inner wall of said cylindrical body, said distal inner wall having a size and shape adapted to induce a first frictional force against the longitudinal friction face, said open distal end having a size, shape, and dimension adapted to minimize morselization of the viscoelastic bone plug piston; and
 (b) plunger means for compressing the viscoelastic bone plug piston within the open distal end of said cylindrical body, said plunger means including a distal surface, a longitudinal surface, and a proximal surface, said plunger means defining a first fluid chamber between said distal surface and the proximal compression face of the viscoelastic bone plug piston, said plunger means further defining a second fluid chamber between said longitudinal surface and the proximal inner wall of said cylindrical body, said plunger means having a size and shape adapted for compressing the viscoelastic bone plug piston into engagement with said distal inner wall of said cylindrical body to substantially prevent disengagement of the viscoelastic bone plug piston from within said open distal end, said plunger means further having a size and shape adapted to induce a pressure gradient across the viscoelastic bone plug piston when said plunger is directed axially so as to cause to separate a viscous fluid therefrom, wherein said cylindrical body further includes means for evacuating the viscous fluid from said cylindrical body, said evacuating means comprising a side opening in the longitudinal surface of said cylindrical body.

10. A syringe assembly as defined in claim 9 wherein said side opening has a size and shape adapted for mounting vacuum means, said vacuum means comprising an elongated tube having a collection chamber integral therewith, said vacuum means adapted for inducing a pressure drop across the viscoelastic bone plug piston so as to ensure the preferential proximal flow of the viscous fluid through said first and said second fluid chambers and into said collection chamber.

11. A syringe assembly for harvesting a viscoelastic bone plug piston comprising:

(a) a cylindrical body having an open distal end, an open proximal end, and a proximal inner wall, said open distal end being adapted to receive a viscoelastic bone plug piston therein, the viscoelastic bone plug piston including a proximal compression face, a longitudinal friction face, and a distal bone pedicle face, the viscoelastic bone plug piston slidably engaging a distal inner wall of said cylindrical body, said distal inner wall having a size and shape adapted to induce a first frictional force against the longitudinal friction face, said open distal end having a size, shape, and dimension adapted to minimize morselization of the viscoelastic bone plug piston; and (b) plunger means for processing the viscoelastic bone plug piston within the open distal end so as to induce the formation of an osteopiston having a short longitudinal friction face, said plunger means including a distal surface, a longitudinal surface, and a proximal surface, said plunger means defining a first fluid chamber between said distal surface and the proximal compression face of the viscoelastic bone plug piston, said plunger means further defining a second fluid chamber between said longitudinal surface and the proximal inner wall of said cylindrical body, said plunger means having a size and shape adapted to compress the viscoelastic bone plug piston into engagement with said distal inner wall of said cylindrical body to substantially prevent disengagement of the osteopiston from within said open distal end, said plunger means further having a size and shape adapted to induce a pressure gradient across the osteopiston when said plunger is directed axially so as to cause to separate a viscous fluid therefrom, wherein said cylindrical body further includes a side opening in the longitudinal surface thereof for evacuating the viscous fluid from said cylindrical body, said side opening having a size and shape adapted for mounting vacuum means, said vacuum means comprising an elongated tube having a collection chamber integral therewith, said vacuum means inducing a pressure drop across the viscoelastic bone plug piston so as to ensure the preferential proximal flow of the viscous fluid through said first and said second fluid chambers and into said collection chamber.

12. A device for harvesting bone, comprising:

a hollow cylindrical rod having a sharpened distal end, a proximal end with a handle thereon, and a chamber therein extending axially between the proximal and distal ends;

a plunger rod inserted into the proximal end of the cylindrical rod, the plunger rod being slidable axially within the chamber, the plunger rod having a substantially flat distal surface for compressing a bone segment received within the distal end of the cylindrical rod;

a sealing support on the proximal end of the hollow cylindrical rod for engaging the plunger rod to establish a hermetic seal therebetween and prevent retrograde flow of air into the chamber from the proximal end of the cylindrical rod; and a side opening in the cylindrical rod communicating with the chamber, the side opening being connectable to a source of vacuum for evacuating fluid from the chamber.

13. The device of claim 12, further comprising a fluid reservoir connectable to the side opening for collecting fluid evacuated from the chamber.

14. A device for harvesting bone, comprising:

a hollow cylindrical rod having a distal end, a proximal end with a handle thereon, and a chamber therein extending axially between the proximal and distal ends;

a plunger rod inserted into the proximal end of the cylindrical rod and slidable axially within the chamber, the plunger rod having a substantially flat distal surface for compressing a bone segment received within the distal end of the cylindrical rod; and a side opening in the cylindrical rod communicating with the chamber, the side opening being connectable to a source of vacuum for evacuating fluid from the chamber.

15. The device of claim 14, further comprising a fluid reservoir connectable to the side opening for collecting fluid evacuated from the chamber.

16. The device of claim 14, wherein the distal end of the cylindrical rod has a sharpened edge.

* * * * *